US012661328B2

(12) United States Patent
Pulley et al.

(10) Patent No.: US 12,661,328 B2
(45) Date of Patent: Jun. 23, 2026

(54) METHODS OF TREATING ANTI-NMDAR-ASSOCIATED NEUROPSYCHIATRIC DISORDERS

(71) Applicant: Vanderbilt University, Nashville, TN (US)

(72) Inventors: Jill M. Pulley, Nashville, TN (US); Jillian P. Rhoads, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 40 days.

(21) Appl. No.: 16/970,654

(22) PCT Filed: Feb. 19, 2019

(86) PCT No.: PCT/US2019/018591
§ 371 (c)(1),
(2) Date: Aug. 18, 2020

(87) PCT Pub. No.: WO2019/161391
PCT Pub. Date: Aug. 22, 2019

(65) Prior Publication Data
US 2020/0368181 A1 Nov. 26, 2020

Related U.S. Application Data

(60) Provisional application No. 62/632,065, filed on Feb. 19, 2018.

(51) Int. Cl.
*A61K 31/13* (2006.01)
*A61P 25/18* (2006.01)
*A61P 37/02* (2006.01)

(52) U.S. Cl.
CPC .............. *A61K 31/13* (2013.01); *A61P 25/18* (2018.01); *A61P 37/02* (2018.01)

(58) Field of Classification Search
CPC ........... A61K 31/13; A61P 25/18; A61P 37/02
See application file for complete search history.

(56) References Cited

U.S. PATENT DOCUMENTS 9,649,266 B2 5/2017 Edelson
2012/0295952 A1 11/2012 Collard et al.

OTHER PUBLICATIONS

Macinko et. al. (Clinical and Experimental Neuroimmunology (2012) 3:116-128) (Year: 2012).*
Kornhuber (Neuroscience Letters (1995) 137-139). (Year: 1995).*
Petri et. al. (Seminars in Arthritis and Rheumatism (2011) 41:194-202). (Year: 2011).*
DeGiorgio et. al. (Nature Medicine (2001) 7:1189-1193). (Year: 2001).*
Of Marcinko et. al. (Clinical and Experimental Neuroimmunology (2012) 3:116-128). (Year: 2012).*
1000 Genomes Project Consortium, Auton et al., "A global reference for human genetic variation", Nature, 2015, vol. 526, No. 7571, pp. 68-74.
Aboujaoude et al., "Memantine augmentation in treatment-resistant obsessive-compulsive disorder: an open-label trial", J Clin Psychopharmacology, 2009, vol. 29, No. 1, pp. 51-55.
Adzhubei et al., "Predicting functional effect of human missense mutations using PolyPhen-2", Curr Protoc Hum Genet, Chapter 7, Unit 7.20, 2013, 41 pages.
Ainiala et al., "The prevalence of neuropsychiatric syndromes in systemic lupus erythematosus", Neurology, 2001, vol. 57, pp. 496-500.
Alizadeh et al., "Effect of Memantine on Cognitive Performance in Patients Under Electroconvulsive Therapy: A Double-Blind Randomized Clinical Trial", Clin Neuropharmacol, 2015, vol. 38, No. 6, pp. 236-240.
Aman et al., "Safety and Efficacy of Memantine in Children with Autism: Randomized, Placebo-Controlled Study and Open-Label Extension", J Child Adolesc Psychopharmacol, vol. 27, No. 5, 2017, pp. 403-412.
Ando et al., "Prevalence of elevated serum anti-N-methyl-D-aspartate receptor antibody titers in patients presenting exclusively with psychiatric symptoms: a comparative follow-up study", BMC Psychiatry, 2016, vol. 16:226, 11 pages.
Arinuma et al., "Association of cerebrospinal fluid anti-NR2 glutamate receptor antibodies with diffuse neuropsychiatric systemic lupus erythematosus", Arthritis Rheum., 2008, vol. 58, No. 4, pp. 1130-1135.
Bai et al. "Chapter 5: Transcriptional Regulation of NMDA Receptor Expression" In: Van Dongen AM, editor. Biol NMDA Recept, 2009, pp. 80-101.
Battista et al., "Pilot trial of memantine in the treatment of post-traumatic stress disorder", Psychiatry, 2007, vol. 70, No. 2, pp. 167-174.
Beneyto et al., "Lamina-specific abnormalities of NMDA receptor-associated postsynaptic protein transcripts in the prefrontal cortex in schizophrenia and bipolar disorder", Neuropsychopharmacol., 2008, vol. 33, No. 9, pp. 2175-2186.
Benseler et al., "Neuropsychiatric involvement in pediatric systemic lupus erythematosus", Lupus, 2007, vol. 16, pp. 564-571.
Berthier et al., "Drug therapy of post-stroke aphasia: a review of current evidence", Neuropsychol Rev., 2011, vol. 21, No. 3, pp. 302-317.
Boada et al., "Antagonism of NMDA receptors as a potential treatment for Down syndrome: a pilot randomized controlled trial", Transl Psychiatry, 2012; 2, e141, 11 pages.
Brey et al., "Neuropsychiatric syndromes in lupus: Prevalence using standardized definitions", Neurology, 2002, vol. 58, No. 8, pp. 1214-1220.

(Continued)

*Primary Examiner* — Marcos L Sznaidman
(74) *Attorney, Agent, or Firm* — MICHAEL BEST & FRIEDRICH LLP

(57) ABSTRACT

The present disclosure is directed to methods for treating a neuropsychiatric disorder associated with expression of autoantibodies to ionotropic glutamate receptor, NMD A 2A (GiuN2A), expression of anti-double-stranded (ds) DNA antibodies that cross react with one or more subunits of the NMD A receptor, or a mutation in the ionotropic glutamate receptor NMD A type subunit 2A (GRIN2A) gene. The methods involve administering a memantine, or a pharmaceutically acceptable salt thereof, to a subject suffering from a neuropsychiatric disorder associated with expression of GluN2A or a mutation in the GRIN2A gene.

9 Claims, 3 Drawing Sheets

(56) References Cited

OTHER PUBLICATIONS

Cacabelos et al., "The glutamatergic system and neurodegeneration in dementia: preventive strategies in Alzheimer's disease", Int J Geriatr Psychiatry., 1999, vol. 14, pp. 3-47.
Carbotte et al., "Prevalence of Cognitive Impairment in Systemic Lupus Erythematosus", J. Nerv. Ment. Dis, 1986, vol. 174, No. 6, pp. 357-364.
Carlomagno et al., "Cognitive impairment in systemic lupus erythematosus: a follow-up study", J Neurol., 2000, vol. 247, No. 4, pp. 273-279.
Chang et al., "Beta-0 thalassemia, a nonsense mutation in man", Proc Natl Acad Sci, 1979, vol. 76, No. 6, pp. 2886-2889.
Chiang et al., "Mammalian microRNAs: experimental evaluation of novel and previously annotated genes", Genes Dev., 2010, vol. 24, No. 10, pp. 992-1009.
Coyle, "NMDA receptor and schizophrenia: a brief history", Schizophr Bulletin, 2012, vol. 38, No. 5, pp. 920-926.
Dalmau et al., "Clinical experience and laboratory investigations in patients with anti-NMDAR encephalitis", Lancet Neurol., 2011, vol. 10, No. 1, pp. 63-74.
Danchenko et al., "Lupus Around the World: Epidemiology of systemic lupus erythematosus: a comparison of worldwide disease burden", Lupus, 2006, vol. 15, No. 5, pp. 308-318.
DeGiorgio et al., "A subset of lupus anti-DNA antibodies cross-reacts with the NR2 glutamate receptor in systemic lupus erythematosus", Nat. Med, 2001, vol. 7, No. 11, pp. 1189-1193.
Denburg et al., "Cognitive Impairment in Systemic Lupus Erythematosus: A Neuropsychological Study of Individual and Group Deficits", J. Clin. Exp. Neuropsychol, 1987, vol. 9, No. 4, pp. 323-339.
Elkon et al., "Nature and functions of autoantibodies", Nature Clinical Practice Rheumatology, 2008, vol. 4, No. 9, pp. 491-498.
Endele et al, "Mutations in GRIN2A and GRIN2B encoding regulatory subunits of NMDA receptors cause variable neurodevelopmental phenotypes", Nat Genet, 2010, vol. 42, No. 11, pp. 1021-1026.
Flicek et al., "Ensembl 2011", Nucleic Acids Research, 2011, vol. 39(Database issue), pp. D800-D806.
Fragoso-Loyo et al., "Serum and cerebrospinal fluid autoantibodies in patients with neuropsychiatric lupus erythematosus. Implications for diagnosis and pathogenesis", PloS One, 2008, vol. 3, No. 10, e3347, 7 pages.
Gaynor et al., "Peptide inhibition of glomerular deposition of an anti-DNA antibody", Proc Natl Acad Sci, 1997, vol. 94, pp. 1955-1960.
Goes et al., "Genome-wide association study of schizophrenia in Ashkenazi Jews", Am J Med Genet B Neuropsychiatr Genet., 2015, vol. 168, No. 8, pp. 649-659.
Grossberg et al., "The safety, tolerability, and efficacy of once-daily memantine (28 mg): a multinational, randomized, double-blind, placebo-controlled trial in patients with moderate-to-severe Alzheimer's disease taking cholinesterase inhibitors", CNS Drugs, 2013, vol. 27, No. 6, pp. 469-478.
Hamosh et al., "Cystic Fibrosis Patients Bearing Both the Common Missense Mutation Gly-vAsp at Codon 551 and the AF508 Mutation Are Clinically Indistinguishable from AF508 Homozygotes, Except for Decreased Risk of Meconium lieus", Am. J. Hum. Genet., 1992, vol. 51, No. 2, pp. 245-250.
Hanly et al., "Prospective analysis of neuropsychiatric events in an international disease inception cohort of patients with systemic lupus erythematosus", Ann Rheum Dis, 2010, vol. 69, pp. 529-535.
Hanly et al., "A Prospective Analysis of Cognitive Function and Anticardiolipin Antibodies in Systemic Lupus Erythematosus", Arthritis Rheum, 1999, vol. 42, No. 4, pp. 728-734.
Hanly et al., "Neuropsychiatric Events at the Time of Diagnosis of Systemic Lupus Erythematosus", Arthritis Rheum, 2007, vol. 56, No. 1, pp. 265-273.
Hanly et al., "Neuropsychiatric Events in Systemic Lupus Erythematosus: Attribution and Clinical Significance", J. Rheumatol, 2004, vol. 31, pp. 2156-2162.
Hanly et al., "Prospective Study of Neuropsychiatric Events in Systemic Lupus Erythematosus", J. Rheumatol, 2009, vol. 36, pp. 1449-1459.
Hanly et al., "Anti-NR2 Glutamate Receptor Antibodies and Cognitive Function in Systemic Lupus Erythematosus", J. Rheumatol., 2006, vol. 33, No. 8, pp. 1553-1558.
Hanly, "The neuropsychiatric SLE SLICC inception cohort study", Lupus, vol. 17, 2008, pp. 1059-1063.
Harel et al, "Neuropsychiatric Manifestations in Pediatric Systemic Lupus Erythematosus and Association with Antiphospholipid Antibodies", J. Rheumatol, 2006, vol. 33, No. 9, pp. 1873-1877.
Hiraki et al., "Clinical and Laboratory Characteristics and Long-Term Outcome of Pediatric Systemic Lupus Erythematosus: A Longitudinal Study", J. Pediatrics, 2008, vol. 152, No. 4, pp. 550-556.
Hochberg, "Updating the American College of Rheumatology Revised Criteria for the Classification of Systemic Lupus Erythematosus", Arthritis Rheum, 1997, vol. 40, No. 9, p. 1725.
Husebye et al., "Autoantibodies to a NR2A peptide of the glutamate/NMDA receptor in sera of patients with systemic lupus erythematosus", Ann Rheum Dis., 2005 vol. 64, No. 8, pp. 1210-1213.
Iizuka et al., "Anti-NMDA receptor antibody-mediated encephalitis/encephalopathy", Rinsho Byori., 2009, vol. 57, No. 3, pp. 252-261.
Ingram, "A Specific Chemical Difference Between the Globins of Normal Human and Sickle-Cell Anemia Haemoglobin", Nature, 1956, vol. 178, No. 4537, pp. 792-794.
Ivanova et al., "NMDA receptor genotypes associated with the vulnerability to develop dyskinesia", Transl Psychiatry, 2012, vol. 2, No. 1, 4 pages.
Kim et al., "The GRIN2B and GRIN2A Gene Variants Are Associated With Continuous Performance Test Variables in ADHD", J Atten Disord, 2020 (published online May 2016), pp. 1538-1546.
Kovacs et al., "Dilemmas in Neuropsychiatric Lupus", Rheum. Dis. Clin. North Am, 1993, vol. 19, pp. 795-814.
Kowal et al, "Cognition and Immunity: Antibody Impairs Memory", Immunity, 2004, vol. 21, No. 2, pp. 179-188.
Krupp et al., "N-terminal domains in the NR2 subunit control desensitization of NMDA receptors", Neuron., 1998, vol. 20, No. 2, pp. 317-327.
Kumar et al., "Predicting the effects of coding non-synonymous variants on protein function using the SIFT algorithm", Nat Protoc., 2009, vol. 4, No. 8, pp. 1073-1082.
Lauvsnes et al., "Association of hippocampal atrophy with cerebrospinal fluid antibodies against the NR2 subtype of the N-methyl-D-aspartate receptor in patients with systemic lupus erythematosus and patients with primary Sjögren's syndrome", Arthritis Rheumatol., 2014, vol. 66, No. 12, pp. 3387-3394.
Levite, "Glutamate receptor antibodies in neurological diseases: anti-AMPA-GluR3 antibodies, anti-NMDA-NR1 antibodies, anti-NMDA-NR2A/B antibodies, anti-mGluR1 antibodies or anti-mGluR5 antibodies are present in subpopulations of patients with either: epilepsy, encephalitis, cerebellar ataxia, systemic lupus erythematosus (SLE) and neuropsychiatric SLE, Sjogren's syndrome, schizophrenia, mania or stroke. These autoimmune anti-glutamate receptor antibodies can bind neurons in few brain regions, activate glutamate receptors, decrease glutamate receptor's expression, impair glutamate-induced signaling and function, activate blood brain barrier endothelial cells, kill neurons, damage the brain, induce behavioral/psychiatric/cognitive abnormalities and ataxia in animal models, and can be removed or silenced in some patients by immunotherapy", J Neural Transmission, 2014 vol. 121, No. 8, pp. 1029-1075.
Liu et al., "Genome-Wide Association Study with DNA Pooling Identifies the Variant rs11866328 in the GRIN2A Gene That Affects Disease Progression of Chronic HBV Infection", Viral Immunol., 2011, vol. 24, No. 5, pp. 397-402.
Mackay, "Lupus brain fog: a biologic perspective on cognitive impairment, depression, and fatigue in systemic lupus erythematosus", Immunol Res., 2015, vol. 63, No. 1-3, pp. 26-37.
Mahdieh et al., "An Overview of Mutation Detection Methods in Genetic Disorders", Iran J. Pedatrics, 2013, vol. 23, No. 4, pp. 375-388.

(56) References Cited

OTHER PUBLICATIONS

Marcinko et al., "Effects of prolonged treatment with memantine in the MRL model of central nervous system lupus", Clin Exp Neuroimmunol., 2012, vol. 3 No. 3, pp. 116-128.
Massardo et al., "Anti-N-methyl-D-aspartate receptor and anti-ribosomal-P autoantibodies contribute to cognitive dysfunction in systemic lupus erythematosus", Lupus, 2015, vol. 24, No. 6, pp. 558-568.
McDevitt et al., "Association between GRIN2A promoter polymorphism and recovery from concussion," Brain Injury, 2015, vol. 29, No. 13-14, pp. 1674-1681.
PatientsLikeMe, "Memantine treatment report", <https://www.patientslikeme.com/treatments/show/81-memantine-side-effects-and-efficacy?brand=false#overview>, review by TooManyRabbits, Dec. 2010, 2 pages.
Mikdashi et al., "Predictors of neuropsychiatric damage in systemic lupus erythemataosus: data from the Maryland lupus cohor", Rheumatology, 2004, vol. 43, pp. 1555-1560.
Minkeviciene et al., "Cognition-enhancing and anxiolytic effects of memantine", Neuropharmacology, 2008, vol. 54, No. 7, pp. 1079-1085.
Miyamoto et al., "Hyperfunction of dopaminergic and serotonergic neuronal systems in mice lacking the NMDA receptor epsilon1 subunit", J Neurosci, 2001, vol. 21, No. 2, pp. 750-757.
Miyoshi et al., "Neuropsychiatric Disorders", Springer, 2010, 346 pages.
Nakamura et al., "Efficacy and safety of memantine in patients with moderate-to-severe Alzheimer's disease: results of a pooled analysis of two randomized, double-blind, placebo-controlled trials in Japan", Expert Opin Pharmacotherapy, 2014, vol. 15, No. 7, pp. 913-925.
Noruzzadeh et al., "Memantine for Prophylactic Treatment of Migraine Without Aura: A Randomized Double-Blind Placebo-Controlled Study", Headache, 2016, vol. 56, No. 1, pp. 95-103.
Olazaran et al., "Cognitive Dysfunction in Systemic Lupus Erythematosus: Prevalence and Correlates", Eur Neurol, 2009, vol. 62, No. 1, pp. 49-55.
OMIM Entry, 138253—Glutamate Receptor, Ionotropic, N-Methyl-D-Aspartate, Subunit 2A; GRIN2A, retrieved from the internet, 2016, <https://omim.org/entry/138253>, 14 pages.
Paoletti et al., "NMDA receptor subunit diversity: impact on receptor properties, synaptic plasticity and disease", Nat Rev Neuroscience, 2013, vol. 14, No. 6, pp. 383-400.
Peyro Saint Paul et al., "Efficacy and safety profile of memantine in patients with cognitive impairment in multiple sclerosis: A randomized, placebo-controlled study", J Neurol Sci. 2016, vol. 363, pp. 69-76.
Pinacho et al., "Analysis of Sp transcription factors in the postmortem brain of chronic schizophrenia: a pilot study of relationship to negative symptoms", J Psychiatr Res., 2013 vol. 47, No. 7, pp. 926-934.
Prickett et al., "Somatic mutation of GRIN2A in malignant melanoma results in loss of tumor suppressor activity via aberrant NMDAR complex formation", J Invest Dermatololgy, 2014, No. 134, vol. 9, pp. 2390-2398.
Pruitt et al., "NCBI Reference Sequences: current status, policy and new initiatives", Nucleic Acids Res., 2009, Database issue, pp. D32-D36.
De Marcaida et al., "Disorders that Mimic Central Nervous System Infections", Neurol Clin, 1999, vol. 17, No. 4, pp. 901-941.
Rossignol et al., "The use of medications approved for Alzheimer's disease in autism spectrum disorder: a systematic review", Front Pediatr., 2014, vol. 2, Article 87, 8 pages.
Sabbadini et al., "Central nervous system involvement in systemic lupus erythematosus patients without overt neuropsychiatric manifestations", Lupus, 1999, vol. 8, No. 1, pp. 11-19.
Ripke et al., "Biological insights from 108 schizophrenia-associated genetic loci", Nature, 2014, vol. 511, No. 7510, pp. 421-427.
Schulz et al., "Neuroprotective strategies for treatment of lesions produced by mitochondrial toxins: implications for neurodegenerative diseases", Neuroscience, 1996, vol. 71, No. 4, pp. 1043-1048.
Schwartz et al., "Memantine as an Augmentation Therapy for Anxiety Disorders", Case Rep Psychiatry, 2012, 3 pages.
Seritan et al., "Memantine for fragile X-associated tremor/ataxia syndrome: a randomized, double-blind, placebo-controlled trial", J Clin Psychiatry, 2014, vol. 75, No. 3, pp. 264-271.
Sharma et al., "Studies of human polyclonal and monoclonal antibodies binding to lupus autoantigens and cross-reactive antigens" Rheumatology, 2003, vol. 42, pp. 453-460.
Sibbitt et al., "The Incidence and Prevalence of Neuropsychiatric Syndromes in Pediatric Onset Systemic Lupus Erythematosus", J. Rheumatol, vol. 29, No. 7, 2002, pp. 1536-1542.
Siddoway et al., "Glutamatergic Synapses: Molecular Organisation", eLS John Wiley & Sons, Ltd, 2011, 9 pages.
Soto et al., "Glutamate receptor mutations in psychiatric and neurodevelopmental disorders", Commun Integr Biol., 2014, vol. 7, No. 1, e27887, 6 pages.
Sun et al. "The Functional and Molecular Properties, Physiological Functions, and Pathophysiological Roles of GluN2A in the Central Nervous System", Mol Neurobiology, 2017, pp. 1008-1021.
Tan et al., "The 1982 Revised Criteria for the Classification of Systemic Lupus Erythematosus", Arthritis Rheum, 1982, vol. 25, pp. 1271-1277.
Taylor et al., "Current and Emerging Techniques for Diagnostic Mutation Detection", Methods Mol Med, 2004, vol. 92, pp. 9-44.
Liang, "The American College of Rheumatology nomenclature and case definitions for neuropsychiatric lupus syndromes", Arthritis Rheum., 1999, vol. 42, No. 4, pp. 599-608.
Turner et al., "GRIN2A: an aptly named gene for speech dysfunction", Neurology, 2015, vol. 84, No. 6, pp. 586-593.
Veerman et al., "Memantine augmentation in clozapine-refractory schizophrenia: a randomized, double-blind, placebo-controlled crossover study", Psychol Med., 2016, vol. 46, No. 9, pp. 1909-1921.
Volkmann et al., "MPX-004 and MPX-007: New Pharmacological Tools to Study the Physiology of NMDA Receptors Containing the GluN2A Subunit", PloS One. 2016, vol. 11, No. 2, p. e0148129, 20 pages.
Wang et al., "Impact analysis of autoantibody level and NR2 antibody level in neuropsychiatric SLE treated by methylprednisolone combined with MTX and DXM intrathecal injection", Cell Biochem Biophys. 2014, vol. 70, No. 2, pp. 1005-1009.
Welter et al., "The NHGRI GWAS Catalog, a curated resource of SNP-trait associations", Nucleic Acids Res., 2014, vol. 42, Database issue, pp. D1001-D1006.
Wishart et al. "DrugBank: a comprehensive resource for in silico drug discovery and exploration", Nucleic Acids Res., 2006, vol. 1, No. 34 (Database issue), pp. D668-D672.
Wu et al., "GRIN2A polymorphisms and expression levels are associated with lead-induced neurotoxicity", Toxicol Ind Health, vol. 33, No. 4, 2017, pp. 323-339.
Xia et al., "Memantine preferentially blocks extrasynaptic over synaptic NMDA receptor currents in hippocampal autapses", J Neurosci, 2010, vol. 30, No. 33, pp. 11246-11250.
Xu et al., "Mutations of N-Methyl D-Aspartate Receptor Subunits in Epilepsy", Neuroscience Bulletin, vol. 34, No. 3, 2018, pp. 549-565.
Yang et al., "Memantine effects on verbal memory in fragile X-associated tremor/ataxia syndrome (FXTAS): a double-blind brain potential study", Neuropsychopharmacol, 2014, vol. 39, No. 12, pp. 2760-2768.
Yoshio et al., "Association of IgG anti-NR2 glutamate receptor antibodies in cerebrospinal fluid with neuropsychiatric systemic lupus erythematosus", Arthritis Rheum., 2006, vol. 54, No. 2, pp. 675-678.
Zhao et al., "Adult AIDS Clinical Trial Group (ACTG) 301 Team. Memantine for AIDS Dementia Complex: Open-Label Report of ACTG 301", HIV Clin Trials, 2010, vol. 11, No. 1, pp. 59-67.
Zhu et al., "Systemic lupus erythematosus with neuropsychiatric manifestation incurs high disease costs: a cost-of-illness study in Hong Kong", Rheumatology, 2009, vol. 48, No. 5, pp. 564-568.
Zimmermann et al., "Global Cognitive Impairment in Systemic Lupus Erythematosus Patients: A Structural MRI Study", Clin Neuroradiol., 2017, vol. 27, pp. 23-29.

(56) References Cited

OTHER PUBLICATIONS

International Search Report and Written Opinion for Application No. PCT/US19/18591 dated May 14, 2019 (13 pages).
Pierson et al., "GRINA2A mutation and early-onset epileptic encephalopathy: personalized therapy with memantine", Annals of Clinical and Translational Neurology, vol. 1, No. 3, 2014, pp. 190-198.
Petri et al., "Memantine in Systemic Lupus Erythematosus: A Randomized, Double-Bold Placebo-Controlled Trial", Seminars in Arthritis and Rheumatism, vol. 41, No. 2, 2011, pp. 194-202.
Olivan-Blazquez et al., "Efficacy of memantine in the treatment of fibromyalgia: A double-blind randomised, controlled trial with 6-month follow-up", Pain, vol. 155, 2014, pp. 2517-2525.
International Preliminary Report on Patentability For Application No. PCT/US2019/018591 dated Aug. 27, 2020 (6 pages).
PatientsLikeMe, "Memantine treatment report", <https://www.patientslikeme.com/treatments/show/81-memantine-side-effects-and-efficacy?brand=false#overview>, review by Daisy1189, Apr. 2010, 2 pages.
PatientsLikeMe, "Memantine treatment report", <https://www.patientslikeme.com/treatments/show/81-memantine-side-effects-and-efficacy?brand=false#overview>, review by MiniRoo/VVV, May 2010, 2 pages.
Ahmad-Sabry, M.-H., et al. "Effects of memantine on pain in patients with complex regional pain syndrome—a retrospective study." Middle East J Anaesthesiol 23.1 (2015): 51-54.
Bhai, S. et al. "A 40-week phase 2B randomized, multicenter, double-blind, placebo-controlled study evaluating the safety and efficacy of memantine in amyotrophic lateral sclerosis." Muscle & nerve 71.1 (2025): 63-72.
Bisaga, A., et al. "A placebo-controlled trial of memantine as an adjunct to injectable extended-release naltrexone for opioid dependence." Journal of Substance Abuse Treatment 46.5 (2014): 546-552.
Boinpally, R., et al. "A novel once-daily fixed-dose combination of memantine extended release and donepezil for the treatment of moderate to severe Alzheimer's disease: two phase I studies in healthy volunteers." Clinical Drug Investigation 35 (2015): 427-435.
Collins, E. D., et al. "The effects of acute pretreatment with high-dose memantine on the cardiovascular and behavioral effects of cocaine in humans." Experimental and Clinical Psychopharmacology 15.3 (2007): 228.
Comer, S. D., et al. "Memantine produces modest reductions in heroin-induced subjective responses in human research volunteers." Psychopharmacology 193 (2007): 235-245.
Ferguson, J. M., et al. "An open-label, flexible-dose study of memantine in major depressive disorder." Clinical neuropharmacology 30.3 (2007): 136-144.
Gonzalez, G., et al. "Memantine improves buprenorphine/naloxone treatment for opioid dependent young adults." Drug and alcohol dependence 156 (2015): 243-253.
Gopaul, D. A. et al "Neuropsychiatric Systemic Lupus Erythematosus: Antibodies Involved, Clinical Characteristics and Treatment." (Sep. 28, 2023) https://www.preprints.org/manuscript/202309.2018/v1 (22 pages).
Kornhuber, J., et al. "Memantine pharmacotherapy: a naturalistic study using a population pharmacokinetic approach." Clinical pharmacokinetics 46 (2007): 599-612.
Krishnan-Sarin, S., et al. "N-methyl-d-aspartate receptor antagonism has differential effects on alcohol craving and drinking in heavy drinkers." Alcoholism: Clinical and Experimental Research 39.2 (2015): 300-307.
Narayanan, B., et al. "Effects of memantine on event-related potential, oscillations, and complexity in individuals with and without family histories of alcoholism." Journal of studies on alcohol and drugs 74.2 (2013): 245-257.
NCT02079246. Long-term Safety and Tolerability of Idalopirdine (Lu AE58054) as Adjunctive Treatment to Donepezil in Patients With Mild-moderate Alzheimer's Disease (STAR Extension) (NCT02079246) Last Update Posted Aug. 10, 2018 (67 pages).
NCT03468543. Study Determining Gastric-Retentive and Modified Release Properties of Prototype Capsules in Healthy Subjects (Terminated) (NCT03468543) Last update posted Jun. 5, 2019 (33 pages).
NDA 21-627. Namenda Tables/Oral Solution (memantine hydrochloride) label information. Accessed on May 19, 2025. Available online at https://www.accessdata.fda.gov/drugsatfda_docs/label/2005/021627lbl.pdf (23 pages).
Nirogi, R., et al. "Effect of concurrent use of memantine on the efficacy of masupirdine (SUVN-502): A post hoc analysis of a phase 2 randomized placebo-controlled study." Neurology and Therapy 11.4 (2022): 1583-1594.
Periclou, A., et al. "Pharmacokinetic study of memantine in healthy and renally impaired subjects." Clinical Pharmacology & Therapeutics 79.1 (2006): 134-143.
Phillips, M. B., et al. "State-specific inhibition of NMDA receptors by memantine depends on intracellular calcium and provides insights into NMDAR channel blocker tolerability." bioRxiv (2024): Apr. 2024 (50 pages).
Swerdlow, N. R., et al. "The effects of memantine on prepulse inhibition." Neuropsychopharmacology 34.7 (2009): 1854-1864.
Szegedi, V., et al. "In vivo evidence for functional NMDA receptor blockade by memantine in rat hippocampal neurons." Journal of neural transmission 117 (2010): 1189-1194.
Thomas, S. J., et al. "Memantine: a review of studies into its safety and efficacy in treating Alzheimer's disease and other dementias." Clinical interventions in aging (2009): 367-377.
Thurtell, M. J., et al. "Crossover trial of gabapentin and memantine as treatment for acquired nystagmus." Annals of neurology 67.5 (2010): 676-680.
Vosburg, S. K., et al. "An evaluation of the reinforcing effects of memantine in cocaine-dependent humans." Drug and alcohol dependence 79.2 (2005): 257-260.
Zhao, Y., et al. "Memantine for AIDS dementia complex: open-label report of ACTG 301." HIV clinical trials 11.1 (2010): 59-67.

* cited by examiner

METHODS OF TREATING ANTI-NMDAR-ASSOCIATED NEUROPSYCHIATRIC DISORDERS

This patent application is the U.S. national stage entry, under 35 U.S.C. § 371, of International Application Number PCT/US2019/018591, filed Feb. 19, 2019, priority to U.S. Provisional Application No. 62/632,065, filed Feb. 19, 2018, which is the entire contents of each of which are hereby incorporated by reference.

TECHNICAL FIELD

The present disclosure is directed to methods for treating a neuropsychiatric disorder associated with expression of autoantibodies to ionotropic glutamate receptor, NMDA 2A (GluN2A), expression of anti-double-stranded (ds) DNA antibodies that cross react with one or more subunits of the NMDA receptor, or a mutation in the ionotropic glutamate receptor NMDA type subunit 2A (GRIN2A) gene.

BACKGROUND

N-methyl-D-aspartate (NMDA) receptors are ionotropic receptors that, when open, allow for the transfer of electrical signals between neurons in the brain and spinal column (Sun et al., *Molecular Neurobiol.,* 54(2): 1008-1021 (2017); Paoletti et al., *Nat. Rev. Neurosci.,* 14(6): 383-400 (2013); and Soto et al., *Commun Integr Biol.,* 7(1):e27887 (2014)). NMDA receptors induce a change in the synaptic transmission which underlies learning and memory, also known as the synaptic plasticity, by mediating the cellular processes critical for synaptic transmission and plasticity.

In mammals, functional NMDA receptors (NMDARs or NRs) are glutamate-gated ion channels that are present at most excitatory mammalian synapses which are comprised of heterotetramers of subunits encoded by three gene families: NR1, NR2 and NR3. The NR1 family consists of one gene with eight isomers, and is an essential structural component found in all tetramers. The NR2 family consists of four genes encoding four GluN2 subunits (GluN2A-D), which contribute to four diheteromeric NMDAR subtypes that have divergent physiological and pathological roles. GluN2A and GluN2B are the two primary types of GluN2 subunits in the forebrain (Sun et al., supra). In the adult brain, GluN2A exists at synaptic sites more abundantly than GluN2B. The NR3 proteins consist of two members (A and B) and function as negative components when included in receptor structures. The composition of different subunits and splicing variants form the primary basis of the functional diversity of NRs (Bai G., Hoffman P. W., "Transcriptional Regulation of NMDA Receptor Expression," In: Van Dongen A M, editor. *Biology of the NMDA Receptor*. Boca Raton (Fla.): CRC Press/Taylor & Francis; Chapter 5 (2009)).

Malfunction of the NRs leads to diseases where synaptic plasticity is lost, such as Alzheimer's disease and mental retardation (Siddoway et al., eds., *Glutamatergic Synapses: Molecular Organisation*, John Wiley & sons, Ltd. (2001)). A role for NMDA receptors in systemic lupus erythematosus (SLE) also has been reported. Neuropsychiatric manifestations and brain atrophy are common severe complications of SLE (Marcinko et al., *Clin. Exp. Neuroimmunol.,* 3(3): 116-128 (2012)). Patients often refer to periods of forgetfulness and confusion that are related to impaired cognition as "lupus brain fog" (Mackay, M., *Immunol. Res.,* 63(1-3): 26-37 (2015)). Some SLE patients also have high levels of autoantibodies directed against an epitope of the GluNR2A subunit (Husebye et al., *Ann., Rheum., Dis.,* 64(8): 1210-1213 (2005)), which is encoded by the GRIN2A gene.

Anti-NR2 antibodies have been found to be positive modulators of NMDA receptor function at low concentrations and increase the size of NMDA receptor-mediated excitatory postsynaptic potentials, but at high concentrations anti-NR2 antibodies are pathogenic as they promote excitotoxicity through enhanced mitochondrial permeability transition (Levite, M., *J. Neural. Transm.* (Vienna), 121(8): 1029-1075 (2014)). Anti-NR2 antibodies have been observed in patients with epilepsy, SLE, neuropsychiatric SLE (NPSLE), memory dysfunction and depression in Sjögren's syndrome, stroke, paraneoplastic encephalitis, Herpes Simplex Virus Encephalitis, cognitive impairment, mania and schizophrenia (Levite, supra).

Control of SLE symptoms typically involves one or more of nonsteroidal anti-inflammatory drugs (NSAIDS), antimalarial drugs (e.g., hydroxychloroquine), corticosteroids (e.g., prednisone), immunosuppressants, and biologics (e.g., belimumab). These therapies, however, have little efficacy in treating the neuropsychiatric manifestations of the disease. Thus, there remains a need for compositions and methods for treating neuropsychiatric diseases mediated by aberrant NMDA activity, such as SLE and NPSLE.

BRIEF SUMMARY OF THE INVENTION

In one aspect, the invention provides a method of treating a neuropsychiatric disorder in a subject comprising administering a therapeutically effective amount of memantine, or a pharmaceutically acceptable salt thereof, to the subject, wherein the subject has a mutation in the ionotropic glutamate receptor NMDA type subunit 2A (GRIN2A) gene.

In another aspect, the invention provides a method of treating a neuropsychiatric disorder in a subject comprising administering a therapeutically effective amount of memantine, or a pharmaceutically acceptable salt thereof, to the subject, wherein the subject expresses autoantibodies to ionotropic glutamate receptor, NMDA 2A (GluN2A) and/or anti-double-stranded (ds) DNA antibodies that cross react with one or more subunits of the NMDA receptor.

The present disclosure also provides a method of treating a neuropsychiatric disorder associated with expression of autoantibodies to ionotropic glutamate receptor, NMDA 2A (GluN2A), in a subject in need of treatment, the method comprising administering to the subject a therapeutically effective amount of memantine or a pharmaceutically acceptable salt thereof.

The present disclosure also provides a method of treating a neuropsychiatric disorder in a subject in need of treatment, the method comprising administering to the subject a therapeutically effective amount of memantine or a pharmaceutically acceptable salt thereof after autoantibodies to ionotropic glutamate receptor, NMDA 2A (GluN2A) and/or anti-double-stranded (ds) DNA antibodies that cross react with one or more subunits of the NMDA receptor are detected in the subject.

The present disclosure further provides a method of treating a neuropsychiatric disorder in a subject in need of treatment, the method comprising administering to the subject a therapeutically effective amount of memantine or a pharmaceutically acceptable salt thereof after a mutation in the ionotropic glutamate receptor NMDA type subunit 2A (GRIN2A) gene is detected in the subject.

DETAILED DESCRIPTION OF THE INVENTION

Figure 1:
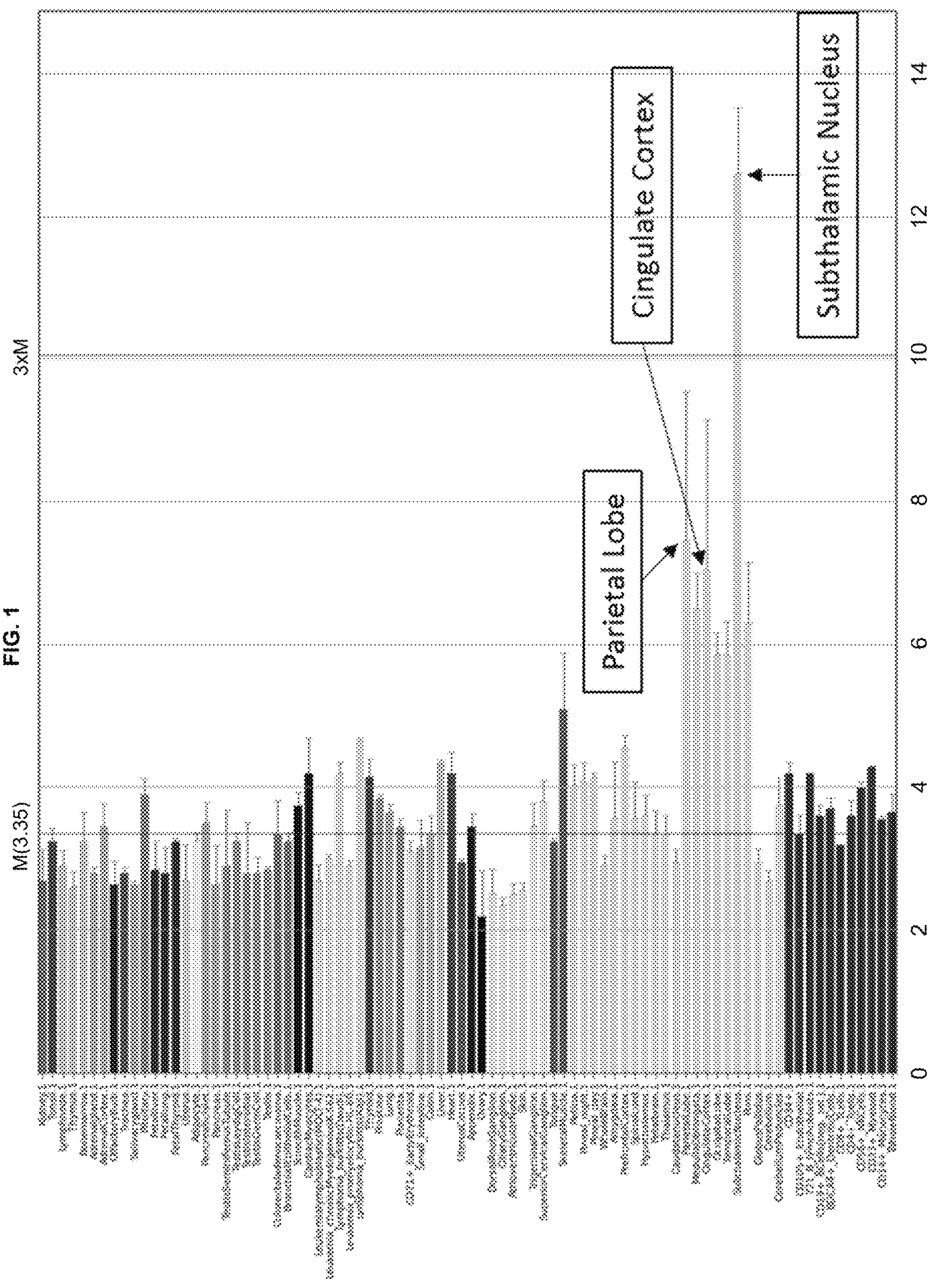
FIG. 1 is a diagram illustrating tissue-specific mRNA expression for the GRIN2A gene.

The present disclosure is predicated, at least in part, on the discovery that neuropsychiatric phenotypes (e.g., seizures, psychosis, anxiety, agitation, cerebrovascular event, lesion of cranial nerves, motor disturbances, quantitative alterations of consciousness, cognitive dysfunction, headache, peripheral neuropathy, malaise, and fatigue) that occur in certain diseases are associated with expression of autoantibodies directed against NMDA receptor components, such as ionotropic glutamate receptor, NMDA 2A (GluN2A). Thus, in one embodiment, the disclosure provides a method of treating a neuropsychiatric disorder associated with expression of autoantibodies to GluN2A in a subject. The method comprises administering a therapeutically effective amount of memantine to a subject comprising a neuropsychiatric disorder associated with expression of autoantibodies to GluN2A, whereby the neuropsychiatric disorder is treated.

Neuropsychiatric Disorders

The terms "neuropsychiatric disorder," "neuropsychiatric syndrome," and "neuropsychiatric symptom," as used herein, refer to a disease, disorder, or condition of affect, cognition, and/or behavior that arises from an overt disorder in cerebral function or from indirect effects of extracerebral disease. Neuropsychiatric disorders typically are characterized by (1) concurrent occurrence of various psychiatric symptoms, (2) cognitive impairment as a core symptom, (3) the possibility of early cerebral symptoms, and (4) occasional resemblance to endogenous psychiatric disorders, which produce symptoms such as, for example, anxiety, neurotic complaint, apathy, mood disorder, hallucinations, delusions, behavioral and personality changes, delirium, and cognitive impairment (dementia) (Miyoshi et al. (eds.), *Neuropsychiatric Disorders*, Springer, 351 pp. (2010)).

The disclosed method may be used to treat any suitable neuropsychiatric disorder, including but not limited to, sleep disorders, addiction (e.g., drug addiction), eating disorders, attention deficit hyperactivity disorder (ADHD), autism, fetal alcohol syndrome, dementia, Parkinson's Disease, Alzheimer's Disease, mood disorders (e.g., bipolar disorder, depression, mania), neurotic disorders (e.g., obsessive-compulsive disorder and anxiety), and schizophrenia. It will also be appreciated that, while not being considered a neuropsychiatric disorder, per se, many diseases have neuropsychiatric components or symptoms, and the disclosed method may also be used to treat such conditions. Examples of such diseases include, but are not limited to, neuropsychiatric systemic lupus erythematosus (NPSLE), systemic lupus erythematosus (SLE) with neurological manifestations, anti-NMDAR encephalitis, anti-NMDAR movement disorders, Sjögren's Syndrome (SS) with neurological manifestations, Creutzfeldt-Jakob disease, myoclonic atonic epilepsy, and postural orthostatic tachycardia syndrome (POTS).

In one embodiment, the disclosed method may be used to treat SLE or NPSLE. SLE is an autoimmune disease that predominantly affects women of child-bearing age. In the United States, SLE is more prevalent among African Americans, Hispanics, and Asians compared to non-Hispanic Caucasians (Danchenko et al., *Lupus,* 15(5): 308-318 (2006)). SLE is characterized by the loss of tolerance to autoantigens and the development of immune complexes that deposit in tissues and cause systemic inflammation. SLE also involves a number of cytokine pathways, including B lymphocyte stimulator (BLys), which promotes B-cell survival and autoantibody production, type I interferon (IFN), which acts as immune adjuvant, and tumor necrosis factor (TNF, which contributes to organ inflammation. Specific subsets of SLE patients present with neuropsychiatric symptoms, such as, for example, mood disorders, seizures, cognitive dysfunction (e.g., difficulty concentrating, difficulty focusing, memory lapses, general confusion, fogginess, aphasia, and the like), acute confusion, neuropathy, and cerebrovascular disease (see, e.g., Hanly et al., *Ann Rheum Dis.,* 69: 5290-535 (2010); Hanly et al., *J. Rheumatol.,* 31: 2156-2162 (2004); Hanly et al., *Arthritis Rheum.,* 56: 265-273 (2007); Hanly, J. G., *Lupus,* 17: 1059-10632 (2008); and Hanly et al., *J Rheumatol,* 36: 1449-1459 (2009)).

Neuropsychiatric lupus (NPSLE) is the least understood yet perhaps one of the most prevalent manifestations of lupus, affecting 14% to over 80% of adults with SLE (Ainiala et al., *Neurology,* 57:496-499 (2001); Brey et al., *Neurology,* 58 (8): 1214-1220 (2002); Hanly et al., *Arthritis Rheum.,* 56 (1): 265-273 (2007); Zhu et al., *Rheumatology* (Oxford), 48 (5): 564-568 (2009), Muscal, E. and Brey, R. L., *Neurol. Clin.,* 28 (1): 61-73 (2010); and Mikdashi, J and Handwerger, B., *Rheumatology,* 43:1555-1560 (2004)) and 22% to 95% of children with SLE (Muscal, supra, Harel et al., *J. Rheumatol.,* 33 (9): 1873-1877 (2006); Sibbitt et al., *J. Rheumatol.,* 29 (7): 1536-1542 (2002); Benseler, S, and Silverman, E., *Lupus,* 16:564-571 (2007); and Hiraki et al., *J. Pediatr.,* 152 (4): 550-556 (2008)). NPSLE can occur independently of active systemic disease and without serologic activity (Sabbadini et al., *Lupus,* 8 (1): 11-19 (1999)) and is associated with increased morbidity and mortality (Ainiala et al., supra; Brey et al., supra; Hanly et al., *Arthritis Rheum.,* 56 (1): 265-273 (2007); Hanly et al., *J. Rheumatol.,* 32 (8): 1459-1456 (2005); and Kovacs et al., *Rheum. Dis. Clin. North Am.,* 19:795-819 (1993)). In 1999, the American College of Rheumatology (ACR) established case definitions for 19 specific neuropsychiatric lupus syndromes, dividing them into two broad categories: central and peripheral (ACR Ad Hoc Committee on Neuropsychiatric Lupus Nomenclature. The American College of Rheumatology nomenclature and case definitions for neuropsychiatric lupus syndromes. *Arthritis Rheum.,* 42:599-608 (1999)). A subject with SLE or NPSLE may exhibit one or more of the following symptoms: aseptic meningitis, cerebrovascular disease, demyelinating syndrome, headache (including migraine and benign, intracranial hypertension), movement disorder (e.g., chorea), myelopathy, seizure disorders, acute confusional state, anxiety disorder, cognitive dysfunction, mood disorder, psychosis, acute inflammatory demyelinating, polyradiculoneuropathy (e.g., Guillain-Barre syndrome), autonomic disorder, mononeuropathy, single/multiplex, myasthenia gravis, neuropathy, cranial, plexopathy, polyneuropathy, and/or aphasia. In NPSLE, cognitive impairment is one of the most common manifestations, with a varying prevalence (Hanly et al., *Arthritis Rheum.,* 42 (4): 728-734 (1999); Carbotte et al., *J. Nerv. Ment. Dis.,* 174: 357-364 (1986); Denburg et al., *J. Clin. Exp. Neuropsychol.,* 9:323-339 (1987); Hanly et al., *J. Rheumatol.,* 33 (8): 1553-1558 (2006); and Olazarán et al., *Prevalence Correlates Eur. Neurol.,* 62 (1): 49-5 (2009)). Seizure and psychosis, however, are the only two NPSLE manifestations that comprise the neurologic component of the ACR classification criteria for SLE (Tan et al., *Arthritis Rheum.,* 25:1271-1277 (1982); Hochberg, M., *Arthritis Rheum.;* 40 (9): 1725 (1997)). It is estimated that 28% to 40% of adult NPSLE manifestations develop before or around the time of the diagnosis of SLE and 63% occur within the first year after diagnosis (Hanly et al., *Arthritis Rheum.,* 56 (1): 265-273 (2007); Kovacs et al., supra; and De Marcaida J A, Reik L Jr., *Neurol. Clin.,* 17 (4): 901-941 (1999)).

NMDA Receptor Autoantibodies and Neuropsychiatric Phenotypes

In one embodiment, the method disclosed herein may be used to treat a neuropsychiatric disorder associated with the presence of autoantibodies directed against one or more subunits of the NMDA receptor, such as, for example, autoantibodies to ionotropic glutamate receptor, NMDA 2A (GluN2A). The term "autoantibody," as used herein, refers to an antibody produced by the immune system of an animal (e.g., a human) that is directed against one or more of the animal's own (or "self") antigens. When present in healthy individuals, autoantibodies may provide a first line of defense against infections, provide housekeeping functions, and/or contribute to immune system homeostasis. In contrast, high-affinity, somatically mutated IgG autoantibodies typically indicate a pathologic process whereby homeostatic pathways related to cell clearance, antigen-receptor signaling, or cell effector functions are disturbed. In some autoimmune disorders, autoantibodies might be present before disease onset and serve as biomarkers which provide an opportunity for diagnosis and therapeutic intervention. In organ-specific autoimmune diseases, such as myasthenia gravis or pemphigus, autoantibodies directly bind to and injure target organs. In systemic autoimmune diseases, such as SLE, autoantibodies react with free molecules, such as phospholipids, as well as cell surface and nucleoprotein antigens, forming pathogenic antigen-antibody (immune) complexes (Elkon, K. and P. Casali, *Nature Clinical Practice Rheumatology,* 4(9): 491-498 (2008)).

In another embodiment, the method may be used to treat a neuropsychiatric disorder associated with the presence of anti-double-stranded (ds) DNA antibodies that cross react with one or more subunits of the NMDA receptor, such as, e.g., NR2A and/or NR2B subunits (Kowal et al., *Immunity,* 21(2): 179-188 (2004)). A subset of lupus anti-DNA antibodies have been identified which cause apoptosis of neurons in vitro in human fetal brain cultures and in vivo following direct injection into mouse brain (see, e.g., DeGiorgio et al., *Nat. Med.,* 7: 1189-1193 (2001); Gaynor et al., *Proc. Natl. Acad. Sci. USA,* 94: 1955-1960 (1997); Sharma et al., Rheumatology (Oxford), 42: 453-463 (2003)).

As discussed above, autoantibodies directed against NMDA receptors (NRs), such as NR2, have been found to be pathogenic at high concentrations, as they promote excitotoxicity through enhanced mitochondrial permeability transition (Levite, supra). Excitotoxicity is the pathological process by which neurons are damaged and killed by the overactivation of glutamate receptors, such as the NMDA and AMPA receptors. Excitotoxicity has been linked to neurodegenerative disorders including Alzheimer's disease and stroke (Mattson et al., Trends Neurosci., 23(5): 222-229 (2000)). In addition to inducing excitotoxicity, anti-NR2 autoantibodies have been shown to induce brain damage, a dramatic decrease of membrane NMDA receptors expressed in hippocampal neurons, and behavioral cognitive impairments in animal models (Levite et al., supra). The concentration of the anti-NMDA antibodies determines whether they exert a positive or negative effect on the activity of the receptors and the survival of neurons (Levite et al., supra).

While serum anti-NR2 antibody levels have not reliably correlated with traditional neuropsychological testing, they have been shown to correlate with spatial memory (Chang et al., supra) as discussed above, and mood disturbances (Omdal et al., *Eur J Neurol.,* 12(5): 392-398 (2005)). Anti-NR2 antibodies have been eluted from SLE brain tissue postmortem, and elevated levels in cerebrospinal fluid have been shown to correlate with severe manifestations of NPSLE, including seizures, acute confusional state, mood and anxiety disorders, psychosis, and cognitive impairment (Arinuma et al., *Arthritis Rheum.,* 58(4):1130-1135 (2008); Fragoso-Loyo et al., *PloS One,* 3(10): e3347 (2008); Yoshio et al., *Arthritis Rheum.,* 54(2): 675-678 (2006); Massardo et al., *Lupus,* 24(6): 558-568 (2015)). Magnetic resonance imaging (MRI) studies have demonstrated correlations between serum anti-NR2 antibody levels and reduced hippocampal volume (Zimmermann et al., *Clin Neuroradiol.,* 27(1): 23-29 (2017); and Lauvsnes et al., *Arthritis Rheumatol* Hoboken N.J., 66(12): 3387-3394 (2014)), and positron emission tomography (PET) has been used to correlate cognitive performance, serum antibody level, and increased hippocampal glucose metabolism with anti-NR2 antibody expression (Mackay, M., *Immunol Res.,* 63(1-3): 26-37 (2015)). Thus, anti-NR2 antibody-mediated damage that involves synaptic plasticity and neuronal excitotoxic apoptosis may be associated with functional consequences in mice and human subjects. Anti-NR2 antibodies also have been observed in patients with epilepsy, memory dysfunction and depression in Sjögren's syndrome, stroke, paraneoplastic encephalitis, Herpes Simplex Virus Encephalitis, cognitive impairment, mania, and schizophrenia (Levite, supra; Ando et al., *BMC Psychiatry,* 16: 226 (2016); and Endele et al., *Nat Genet.,* 42(11): 1021-1026 (2010)).

More severe neurological phenotypes manifesting within various diseases, can arise from the combination of compromised blood-brain barrier function and circulating anti-NMDAR autoantibodies. Decreased blood-brain barrier integrity may generally constitute a major risk factor for detrimental effects of peripheral antibodies against central nervous system epitopes, potentially significant across a range of diseases exhibiting more severe neuropsychiatric symptoms.

Autoantibodies directed against specific components of NR2, such as ionotropic glutamate receptor, NMDA 2A (GluN2A), have been implicated in the development of NPSLE and other neuropsychiatric phenotypes of SLE (see, e.g., Wang et al., *Cell Biochem Biophys.,* 70(2): 1005-1009 (2014); Husebye et al, supra; Hirohata et al., *Arthritis Res Ther.,* 16(2):R77 (2014); Chang et al., *EBioMedicine,* 2(7): 755-764 (2015)), as well as anti-NMDA receptor encephalitis, which is characterized by neurological symptoms such as impaired cognition, memory deficits, psychosis, language disintegration, and aphasia (see, e.g., Iizuka T, Hara A., *Rinsho Byori,* 57(3): 252-261 (2009); and Dalmau et al., *Lancet Neurol.,* 10(1): 63-74 (2011)).

GluN2A, which is the protein encoded by the GRIN2A gene, is part of a glutamate-gated calcium/magnesium ion channel involved in long-term potentiation, which is an activity-dependent increase in the efficiency of synaptic transmission thought to underlie certain kinds of memory and learning (Pruitt et al., *Nucleic Acids Res.,* 37: D32-36 (2009)). Physiological and genetic evidence implicate GluN2A-containing receptors in susceptibility to autism, schizophrenia, childhood epilepsy, and neurodevelopmental disorders such as Rett Syndrome (Volkmann et al., *PloS One,* 11(2): e0148129 (2016)). The GRIN2A gene is expressed in virtually every human tissue, as illustrated in FIG. 1. Expression is highest in the brain, especially the subthalamic nucleus (muscular response), cingulate cortex (learning and memory), and parietal lobe (language processing) (Wu et al., *Nucleic Acids Res.,* 41: D561-565 (2013). Mutations in GRIN2A are associated with focal epilepsy with speech disorder, with or without mental retardation (FESD), lead-induced neurotoxicity, increased susceptibility to attentional impairment in ADHD patients, tardive dyskinesia, depression, disruptive behavior, and longer recovery times from concussions (Wu et al., *Toxicology and Industrial Health,* 33(4): 332-339 (2016); Kim et al., *Journal of Attention Disorders* (2016), DOI: 10.1177/1087054716649665; Ivanova et al., *Transl Psychiatry,* 2(1): e67 (2012); McDevitt et al., *Brain Inj.,* 29(13-14):1674-1681 (2015) OMIM Entry—*138253—Glutamate Receptor, Ionotropic, N-Methyl-D-Aspartate, Subunit 2a; GRIN2A; and OMIM Entry—#245570—Epilepsy, Focal, With Speech Disorder And With Or Without Mental Retardation; FESD).

In some embodiments, the disclosed method comprises obtaining a sample from a subject having a neuropsychiatric disorder and detecting autoantibodies to ionotropic glutamate receptor, NMDA 2A (GluN2A) in the sample, and/or anti-double-stranded (ds) DNA antibodies that cross react with one or more subunits of the NMDA receptor in the sample. The terms "sample," "biological sample," and "test sample" are used interchangeably herein and refer to a substance obtained from an animal suspected of having a neuropsychiatric disorder associated with expression of GluN2A autoantibodies. In other words, the sample is suspected of containing autoantibodies to GluN2A. The sample may be obtained or derived from any suitable subject. In one embodiment, the subject may be an animal, such as a mammal (e.g., a human). In addition to expressing autoantibodies to GluN2A, the subject may exhibit one or more of the following symptoms: seizures, psychosis, a cerebrovascular event, lesion of cranial nerves, motor disturbances, quantitative alterations of consciousness, cognitive dysfunction (e.g., difficulty concentrating, difficulty focusing, memory lapses, general confusion, fogginess, aphasia, and the like), acute confusion, headache, peripheral neuropathy, pain, fibromyalgia, changes in disease monitoring modalities (e.g., magnetic resonance imaging (MRI), electroencephalography (EEG), and electromyoneurography (ENMG)), and/or fatigue.

In embodiments where the subject is a human, the sample may be a human bodily substance (e.g., blood, serum, plasma, urine, saliva, sweat, sputum, semen, mucus, lacrimal fluid, lymph fluid, amniotic fluid, interstitial fluid, lung lavage, cerebrospinal fluid, feces, tissue, an organ, and the like). Human tissues may include, but are not limited to, nervous tissue, skeletal muscle tissue, liver tissue, lung tissue, kidney tissue, myocardial tissue, brain tissue, bone marrow, cervix tissue, and the like. The sample may be a liquid sample, a liquid extract of a solid sample, a fluent particulate solid, or fluid suspension of solid particles.

Autoantibodies to GluN2A or anti-dsDNA antibodies may be detected in the sample using any suitable method known in the art for detecting antibodies. Such methods include, for example, enzyme-linked immunosorbent assay ELISA, radioimmunoassays, Western blot, immunohistochemistry (IHC), immunocytochemistry (ICC), flow cytometry, fluorescence-activated cell sorting (FACS), immunoprecipitation, enzyme linked immunospot (ELISPOT) assay, and the like (see, e.g., Wild, D., ed., *The Immunoassay Handbook,* $4^{th}$ Edition, Elsevier Science (2013)). In some embodiments, the antibodies are to the NR2A subunit(s) DWDYS (residues 283-287) and/or DWEYS of NMDAR detected by ELISA.

In other embodiments, the disclosed method comprises obtaining a sample from a subject having a neuropsychiatric disorder and detecting a mutation (e.g., deletion, insertion, or substitution of one or more nucleic acid sequences) in the GRIN2A gene in the sample. A mutation in the GRIN2A gene may be detected using any suitable technique known in the art. Such techniques include, but are not limited to, direct DNA sequencing, DNA hybridization and/or restriction enzyme digestion, polymerase chain reaction (PCR)-based methods (e.g., RT-PCR, multiplex PCR, nested PCR, real-time PCR), DNA microarrays, multiplex ligation-dependent probe amplification (MLPA), single strand conformational polymorphism (SSCP), denaturing gradient gel electrophoresis (DGGE), heteroduplex analysis, restriction fragment length polymorphism (RFLP) analysis, and next generation sequencing. Methods for detecting genetic mutations are described further in, e.g., Mahdieh, N. and B. Rabbani, *Iran J Pediatr.,* 23(4): 375-388 (2013); Taylor, C. F. and G. R. Taylor, *Methods Mol. Med.,* 92: 9-44 (2004); and Green, M. and J. Sambrook (eds.), *Molecular Cloning: A Laboratory Manual,* $4^{th}$ Edition, Cold Spring Harbor Laboratory Press (2012).

Any mutation in the GRIN2A gene that impairs or obliterates the function of the GluN2A protein encoded thereby may be detected in accordance with the disclosed method. As discussed above, mutations in GRIN2A are associated with focal epilepsy with speech disorder, and somatic mutations in GRIN2A have been identified in cutaneous malignant melanoma patients (see, e.g., Prickett et al., *J Invest Dermatol.,* 134(9): 2390-2398 (2014)), and the disclosed method may be used to detect any of these known GRIN2A mutations. In other embodiments, one or more single nucleotide polymorphisms (SNPs) in the GRIN2A gene associated with a neuropsychiatric condition or phenotype may be detected by the disclosed method. The term "single nucleotide polymorphism," as used herein, refers to is a variation in a single nucleotide that occurs at a specific position in the genome, where each variation is present to some appreciable degree within a population (e.g., >1%). SNPs often underlie differences disease susceptibility, and a wide range of human diseases result from SNPs (e.g., sickle-cell anemia, β-thalassemia and cystic fibrosis) (Ingram, V. M., *Nature,* 178 (4537): 792-794 (1956); Chang, J. C., Kan, Y. W., *Proc. Natl Acad. Sci. USA,* 76 (6): 2886-2889 (1979); and Hamosh et al., *American Journal of Human Genetics,* 51(2): 245-250 (1992)). The disclosed method may be used to detect anyone of the following SNPs in GRIN2A: T141M (reference SNP cluster ID (rs) 78631453), V967L (rs61731465), N1076K (rs61758995), and/or rs524991 (Hammer et al., Mol Psychiatry, 19(10): 1143-9 (2014)), each of which creates a missense mutation in GRIN2A. In one embodiment, the mutation in the GRIN2A gene is a SNP that results in a T141M amino acid substitution in GluN2A.

Memantine

The disclosed method of treating a neuropsychiatric disorder in a subject comprises administering a therapeutically effective amount of memantine to the subject. As used herein, the terms "treatment," "treating," and the like refer to obtaining a desired pharmacologic and/or physiologic effect, e.g., inhibiting or preventing a neuropsychiatric disorder. Preferably, the effect is therapeutic, i.e., the effect partially or completely cures a disease and/or adverse symptom attributable to the disease. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of memantine to elicit a desired response in the individual. The dose of memantine required to achieve a particular therapeutic effect (i.e., inhibition of neuropsychiatric symptoms) will vary based on several factors including, but not limited to, the administration route of memantine, the specific disease or disorder being treated, and the stability of memantine in the patient. One of ordinary skill in the art can readily determine an appropriate memantine dose range to treat a patient having a particular neuropsychiatric disease or disorder based on these and other factors that are well known in the art.

Memantine (1-amino-3,5-dimethyladamantane), marketed as a hydrochloride salt under the brand name NAMENDA® (Allergan USA, Inc., Irvine, CA), is approved in the U.S. for the treatment of moderate to severe dementia in Alzheimer's disease. Memantine is an amantadine derivative with low to moderate-affinity for NMDA receptors having the following structural formula:

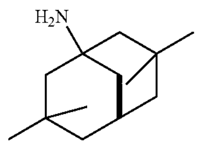

Memantine functions through uncompetitive NMDA receptor antagonism, binding preferentially to the NMDA receptor-operated cation channels (Wishart et al., *Nucleic Acids Res.,* 34: D668-672 (2006)). Prolonged increased levels of glutamate in the brain of demented patients are sufficient to counter the voltage-dependent block of NMDA receptors by $Mg^{2+}$ ions and allow continuous influx of $Ca^{2+}$ ions into cells, ultimately resulting in neuronal degeneration. Studies suggest that memantine binds more effectively than $Mg^{2+}$ ions at the NMDA receptor, and thereby effectively blocks the prolonged influx of $Ca^{2+}$ ions through the NMDA channel while preserving the transient physiological activation of the channels by higher concentrations of synaptically released glutamate (Wishart et al., supra). As such, memantine protects against chronically elevated concentrations of glutamate. Memantine has no affinity for γ-aminobutyric acid (GABA), benzodiazepine, dopamine, adrenergic, histamine, or glycine receptors, or for voltage-dependent calcium, sodium, or potassium channels. Memantine has been characterized as a relative specific inhibitor for extrasynaptic NMDA receptors at low micromolar range (Xia et al., *J. Neurosci. Off J. Soc. Neurosci.,* 30(33): 11246-11250 (2010)), and blocks extrasynaptic NMDA receptor-induced signaling, which is believed to promote cell survival.

In the context of this disclosure, memantine may be administered in the form of a pharmaceutically acceptable salt. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. Salts may be commercially available, or may be prepared during the final isolation and purification of the compounds, or separately by reacting the amino group of memantine with a suitable acid. For example, memantine may be dissolved in a suitable solvent, such as but not limited to methanol and water and treated with at least one equivalent of an acid, such hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. In some embodiments, memantine is administered as a memantine hydrochloride salt.

In one embodiment, the therapeutically effective amount of memantine is administered to the subject in the form of composition comprising memantine and a carrier (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the therapeutically effective amount of memantine. Any suitable carrier can be used within the context of the disclosure, and such carriers are well known in the art. The choice of carrier will be determined, in part, by the particular use of the composition (e.g., administration to an animal) and the particular method used to administer the composition. The composition optionally can be sterile. The composition can be frozen or lyophilized for storage and reconstituted in a suitable sterile carrier prior to use. Suitable compositions include aqueous and non-aqueous isotonic sterile solutions, which can contain anti-oxidants, buffers, suspending agents, solubilizers, thickening agents, stabilizers, and/or preservatives. The compositions can be generated in accordance with conventional techniques described in, e.g., *Remington: The Science and Practice of Pharmacy,* 21st Edition, Lippincott Williams & Wilkins, Philadelphia, PA (2001).

A typical dose of memantine can be, for example, in the range of 1 μg to 50 mg; however, doses below or above this exemplary range are within the scope of the invention, such as up to 60 mg. A daily dose of memantine can be from about 1 μg to about 60 mg or 1 μg to about 40 mg (e.g., about 1.5 μg, about 5 μg, about 10 μg, about 50 μg, about 100 μg, about 500 μg, about 1 mg, about 5 mg, about 10 mg, about 20 mg, about 30 mg, about 40 mg, about 50 mg, about 60 mg, or a range defined by any two of the foregoing values), from about 500 μg to about 30 mg (e.g., about 600 μg, about 700 μg, about 800 μg, about 900 μg, about 15 mg, about 25 mg, or a range defined by any two of the foregoing values), about 5 mg to about 60 mg, about 5 mg to about 40 mg, from about 5 mg to about 20 mg (e.g., about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or a range defined by any two of the foregoing values), or about 20 mg to about 40 mg. Therapeutic efficacy can be monitored by periodic assessment of treated patients. For repeated administrations over several days or longer, depending on the condition, the treatment can be repeated until a desired suppression of disease symptoms occurs. However, other dosage regimens may be useful and are within the scope of the disclosure.

Memantine can be administered to a subject (e.g., a human) using standard administration techniques, including oral, intravenous, intraperitoneal, subcutaneous, pulmonary, transdermal, intramuscular, intranasal, buccal, sublingual, rectal, vaginal, or suppository administration. Memantine may be administered alone or in combination with other drugs or therapies (e.g., as an adjuvant). For example, other drugs or therapies for the treatment neuropsychiatric disorders, such as NPSLE, can be used. Such drugs or therapies include antidepressants (sertraline/ZOLOFT™), benzodiazepines (e.g., alprazolam/XANAX®) stimulants (e.g., methylphenidate/RITALIN®), antipsychotics (aripiprazole/ABILIFY®), nonbenzodiazepine sleep aids (e.g., eszopiclone/LUNESTA®), and psychiatric therapy (e.g., cognitive behavioral therapy). In embodiments where the disclosed method is used to treat neuropsychiatric symptoms associated with a disease (e.g., Sjögren's Syndrome or SLE), as opposed to a disease caused by neuropsychiatric dysfunction per se, memantine can be administered in combination with other drugs or therapies used to treat that disease. For example, in the case of Sjögren's Syndrome, memantine may be administered in combination with nonsteroidal anti-inflammatory drugs (NSAIDs), cyclosporine, and/or pilocarpine.

The following examples further illustrate the invention but, of course, should not be construed as in any way limiting its scope.

Example 1

This example demonstrates a phenome-wide association study (PheWAS) to identify links between mutations in the GRIN2A gene and phenotypes that lack effective treatments.

PheWAS is a systematic and efficient approach to elucidate novel disease-variant associations and pleiotropy using de-identified human genetic data tied to robust, de-identified electronic medical records. A PheWAS analysis with respect to the GRIN2A gene was performed as described in U.S. Provisional Patent Application No. 62/479,808 (filed Mar. 31, 2017). Briefly, the Illumina INFINIUM® Exomechip (Illumina, Inc., San Diego, CA) contains approximately 250,000 coding variants across the protein coding regions of the human genome. The coding variants were discovered through exome and whole genome sequencing in more than 12,000 individuals. The Exomechip was designed to serve as an intermediate step between current genotyping arrays, which are designed to study common variants, and exome sequencing, which can discover rare variants. Nearly all non-synonymous, splice- and stop-altering variants detected in an average genome through exome sequencing are included on the Exomechip. The Exomechip also includes single nucleotide polymorphisms (SNPs) with known disease associations as well as unpublished associations from consortia working on diabetes, blood lipids, blood pressure, lung function, myocardial infraction, anthropometric traits, psychiatric traits, Crohn's disease, and age related macular degeneration. Approximately 35,000 subjects in Vanderbilt University's BioVU DNA databank have genotyping data on this platform. Using this platform, relevant SNPs for the GRIN2A gene were identified and are listed in Table 1.

TABLE 1

| SNP | rsID | Mutation | SIFT Score | Polymorphism Phenotyping v2 (PP2) Score | Exome Variant Allele Frequency (VAF)* | Variant Frequency** | Populations with Highest VAF |
|---|---|---|---|---|---|---|---|
| T141M | rs78631453 | missense | 0.020 | 0.021 | 0.001564 | 0.0003862 | Ashkenazi Jewish (.003707) |
| V967L | rs61731465 | missense | 0.96 | 0.005 | 0.009737 | 0.007962 | South Asian (.008058) |
| N1076K | rs61758995 | missense | 0.09 | 0.699 | 0.007098 | 0.006778 | European (Non-Finnish) |

*variant allele frequency (VAF) reflects the VAF in the Exomechip European ancestry population
**variant allele frequency from genomAD European (Non-Finnish) population (December 2016)

Sorting Intolerant from Tolerant (SIFT) scores at or below 0.05 are considered to be deleterious; those above 0.05 are considered to be tolerated (Kumar et al., *Nat. Protoc.,* 4(7): 1073-1081 (2009)). Polymorphism Phenotyping v2 (Polyphen2 or PP2) scores below 0.447 are considered benign: those higher than 0.908 are considered probably damaging; and those in between possibly damaging (Adzhubei et al., "Predicting Functional Effect of Human Missense Mutations Using PolyPhen-2," *Curr Protoc Hum Genet., Unit* 7.20. (2013)).

All three alleles identified on the PheWAS chip are very rare. The T141M/rs78631453 mutation lies in the N-terminal leucine/isoleucine/valine-binding protein (LIVBP)-like domain of the NR2 subunit. The LIVBP-like domain, along with the four amino acids immediately preceding the first transmembrane domain, flank the putative agonist-binding domain and control the glycine-independent desensitization of the NR2 subunits (Krupp et al., *Nat. Protoc.,* 4(7): 1073-1081 (2009)). The other two mutations fall into the C-terminal domain, similar to that of GluNR2B3.

Only the N1076K/rs61758995 mutation was predicted to possibly be damaging (PP2 score=0.699). Although there are no biochemical enzyme kinetics available for GluN2A-containing NMDA receptors with this mutation, the change in charge, along with homology information, indicated it will most likely reduce the function of the receptor.

Linkage disequilibrium data for the SNPs above, in the populations in which they are most prominent, indicated that the V967L/rs61731465 mutation is linked with the SNP rs147419689 (c.*2236G>A) in British ($r^2$=1.000) and Finnish ($r^2$=0.497) populations, and the SNP rs75272984 (c.*121G>T) in Italians ($r^2$=0.498) (Flicek et al., *Nucleic Acids Res.,* 39: D800-806 (2011); and 1000 Genomes Project Consortium, Auton et al., *Nature,* 526(7571): 68-74 (2015)). Both of these variants are in the 3' untranslated region (UTR) of GRIN2A, known to be important in gene regulation. Binding of microRNAs to specific 3' UTR binding sites on mRNA can down regulate gene expression. Both 3' UTR SNPs are located in potential (and poorly conserved) microRNA binding sites (Chiang et al., *Genes Dev.,* 24(10): 992-1009 (2010)).

The N1076K mutation also has been linked to two SNPs in the 3' UTR in Utah residents of European descent: rs192548671 (c.*8396T>C, $r^2$=1.000) and rs551347981 (c.*7084T>C, $r^2$=0.497) (Flicek et al., supra, and 1000 Genomes Project Consortium, supra). The former SNP is found in three different poorly conserved microRNA binding sites.

None of the three SNPs found on this platform have been associated in the literature with any specific phenotypes to date. As discussed above, most reported mutations in GRIN2A are primarily associated with focal epilepsy with speech disorder with or without mental retardation. Speech disorder has also been found to occur in the absence of epilepsy among individuals with GRIN2A mutations, reinforcing its importance in motor speech function (Turner et al., *Neurology,* 84(6): 586-593 (2015)). For mutated proteins that underwent functional studies, most exhibited little to no function. Phenotypes found in the NHGRI-EBI Catalog of published genome-wide association studies (NHGRI-EBI GWAS) associated with the GRIN2A gene that also appeared in the PheWAS results described above, either as a direct phenotype match or as a related phenotype, are set forth in Table 2.

TABLE 2

| Condition | PheWAS Code | rsID | SNP | P value | Odds Ratio | Case Carriers | Total Cases |
|---|---|---|---|---|---|---|---|
| Schizophrenia | 295.1 | rs61731465 | V967L | 0.01693 | 2.99 | 5 | 81 |
| Viral hepatitis | 070 | rs61731465 | V967L | 0.03329 | 0.29 | 3 | 518 |

The above results are consistent with growing evidence in support of the hypothesis that hypofunction of NMDA receptors and anti-NMDA receptor antibodies are involved in the pathophysiology of schizophrenia (see, e.g., Sun et al., supra, Ando et al., supra, Endele et al., supra, Coyle J T., *Schizophr Bull.,* 38(5): 920-926 (2012); Welter et al., *Nucleic Acids Res.,* 42: D1001-1006 (2014); Schizophrenia Working Group of the Psychiatric Genomics Consortium: Biological insights from 108 schizophrenia-associated genetic loci, *Nature,* 511(7510): 421-427 (2014); Goes et al., *Am. J. Med. Genet. B Neuropsychiatr Genet.,* 168(8): 649-659 (2015); Miyamoto et al., *J. Neurosci. Off. J. Soc. Neurosci.,* 21(2): 750-757 (2001); Pinacho et al., *J. Psychiatr. Res.,* 47(7):926-934 (2013); and Beneyto, M., Meador-Woodruff J. H., *Neuropsychopharmacol.,* 33(9): 2175-2186 (2008)), and possibly Hepatitis B (see, e.g., Welter et al., supra, and Liu et al., *Viral Immunol.,* 24(5): 397-402 (2011)).

Example 2

This example describes new GRIN2A SNPs associated with particular diseases.

Figure 2:
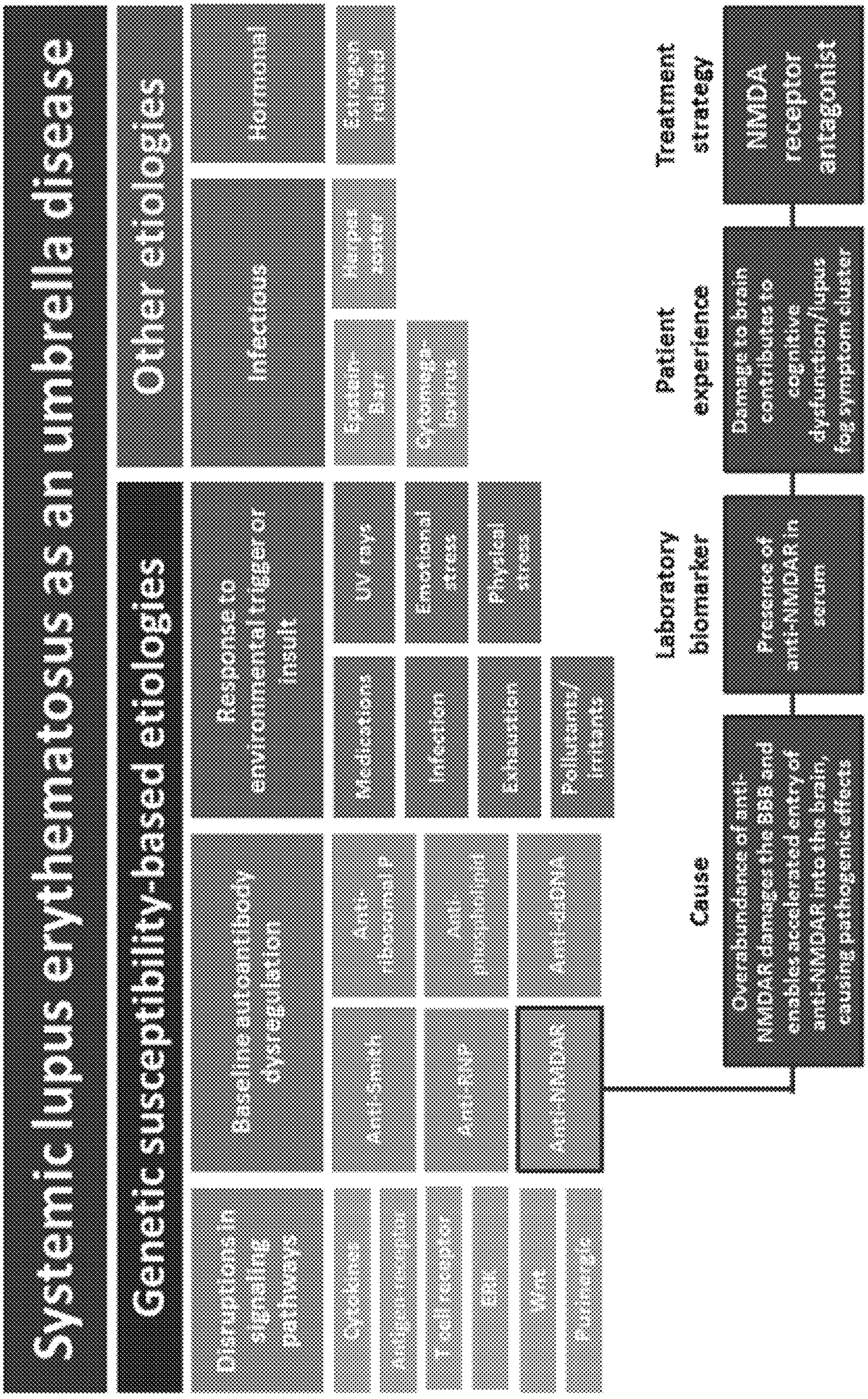
FIG. 2 is a diagram illustrating a precision indication for anti-NMDAR associated NPSLE/lupus fog.

The PheWAS analysis described in Example 1 revealed associations between the three SNPs and three disease clusters: autoimmune disorders, sleep disorders, and neurological disorders. These potentially novel associations are presented in Tables 3-5 below. Moreover, manual reviews of T141 carriers with lupus revealed evidence of NPSLE in 5 of 6 cases analyzed, and language cognitive symptoms/experiences were reported by 67 of 82 participants in a survey of lupus patients. Thus, for patients with SLE or Neuropsychiatric SLE that exhibit cognitive impairment and have high levels of anti-GluNR2 antibodies, a GluN2A antagonist, such as memantine, may be an ideal candidate drug. This precision indication for anti-NMDAR associated NPSLE or "lupus fog" is illustrated further in FIG. 2.

TABLE 3

| Autoimmune and Related Disorders | | | | | | | |
|---|---|---|---|---|---|---|---|
| Condition | PheWAS Code | rsID | SNP | P Value | Odds Ratio | Case Carriers | Total cases |
| Lupus | 695.4 | rs78631453 | T141M | 5.1E−05 | 6.21 | 6 | 462 |
| Systemic lupus erythematosus | 695.42 | rs78631453 | T141M | 2.8E−05 | 6.65 | 6 | 434 |

TABLE 3-continued

| Autoimmune and Related Disorders | | | | | | | |
|---|---|---|---|---|---|---|---|
| Condition | PheWAS Code | rsID | SNP | P Value | Odds Ratio | Case Carriers | Total cases |
| Malaise and fatigue | 798 | rs78631453 | T141M | 9.4E−4 | 5.64 | 4 | 245 |
| Polymyalgia Rheumatica | 717 | rs78631453 | T141M | 2.8E−3 | 5.16 | 4 | 418 |

TABLE 4

| Sleep Disorders | | | | | | | |
|---|---|---|---|---|---|---|---|
| Condition | PheWAS Code | rsID | SNP | P Value | Odds Ratio | Case Carriers | Total cases |
| Sleep disorders | 327 | rs78631453 | T141M | 4.5E−04 | 2.79 | 15 | 2007 |
| Cataplexy and narcolepsy | 347 | rs61758995 | N1076K | 4.2E−03 | 8.63 | 2 | 19 |

TABLE 5

| Neurological Disorders (including degeneration) | | | | | | | |
|---|---|---|---|---|---|---|---|
| Condition | PheWAS Code | rsID | SNP | P Value | Odds Ratio | Case Carriers | Total cases |
| Cerebral edema and compression of brain | 348.2 | rs78631453 | T141M | 5.0E−04 | 4.56 | 6 | 449 |
| Spinocerebellar disease | 334.1 | rs61758995 | N1076K | 5.3E−04 | 6.19 | 4 | 49 |
| Aphasia | 292.11 | rs78631453 | T141M | 7.2E−03 | 5.05 | 3 | 200 |
| Degenerative disease of the spinal cord | 334 | rs61758995 | N1076K | 0.0158 | 2.13 | 11 | 385 |
| Other headache syndromes | 339 | rs61758995 | N1076K | 0.01674 | 5.86 | 2 | 26 |
| Other conditions of brain, NOS | 348.9 | rs61731465 | V967L | .02095 | 0.35 | 5 | 753 |
| Generalized convulsive epilepsy | 345.11 | rs78631453 | T141M | .02416 | 3.39 | 4 | 365 |

The GRIN2A SNP associations described above are consistent with studies showing that sleep, and neurological phenotypes may be associated with GRIN2A mutations that directly or indirectly reduce GluN2A protein function (see, e.g., Ying et al., *Exp Neurol.,* 159(2): 409-418 (1999); Babb et al., *Epilepsia,* 41 Suppl 6: S76-81 (2000); Sakamoto et al., *Brain Res Mol Brain Res,* 102(1-2):113-117 (2002); Endele et al., supra; McDevitt et al., supra; Sun et al., supra; Carvill et al., supra; Sultana et al., *J. Neurosci. Res.,* 88(3): 469-477 (2010); and Beneyto, M., Meador-Woodruff J. H., *Neuropsychopharmacol.,* 33(9): 2175-2186 (2008)).

Example 3

Clinical Trial Design for Memantine for the Treatment of Cognitive Impairment in Systemic Lupus Erythematosus A phenome-wide association study (PheWAS) identified an association between a variant in the human gene for the N2A subunit of the N-methyl-D-aspartate (NMDA) receptor, GRIN2A, and Systemic Lupus Erythematosus (SLE). A single nucleotide polymorphism (SNP) in this gene encodes for increased NMDA receptor activity. Based on the potential function of the associated SNP and published literature, alterations in SNP function signaling may underlie a cluster of symptoms. The objective of this study is to evaluate the safety, tolerability and efficacy of memantine, an NMDA receptor antagonist, in a precise patient subset with SLE. Participants will complete a full 14-week clinical trial, receiving either memantine or a placebo. Participants' blood will be drawn to test for various antibodies as well as organ function. Patients' urine will also be collected to assess organ function and pregnancy for females at a number of specific time points. The overall goal is to develop a safe and inexpensive therapeutic approach to reduce debilitating cognitive symptoms in a precisely selected SLE sub-population.

Study Design

Study Type: Interventional (Clinical Trial)

Estimated Enrollment: 144 participants

Allocation: Randomized

Intervention Model: Parallel Assignment

Intervention Model Description: Double-blind, randomized, placebo-controlled

Masking: Quadruple (Participant, Care Provider, Investigator, Outcomes Assessor)

Primary Purpose: Treatment

Memantine Treatment Group.

At randomization, subjects will receive 5 mg memantine twice per day for one week. They will escalate their dose to 10 mg twice per day for one week, then 10 mg in the morning and 20 mg at night for one week, and finally 20 mg twice per day for three weeks. Maximum tolerated will be determined at this time and this dose will be continued for an additional six weeks Placebo Group.

At randomization, subjects will receive one matching placebo capsule twice per day for one week. They will also take one matching placebo capsule twice per day for the next week (week 2), then one matching placebo capsule in the morning and two capsules at night for one week (week three), and finally two capsules twice per day for three weeks (weeks 4-6). Maximum tolerated number of capsules will be determined at this time and this dose will be continued for an additional six weeks.

Primary Outcome Measures:

1. Repeatable Battery for Assessment of Neuropsychological Status (RBANS) Total Index Score at endpoint (Visit 4) [Time Frame: 12 weeks]

RBANS is a widely used psychiatric tool that objectively measures cognitive impairment. It is comprised of 12 subtests and takes approximately 30 minutes. For scoring, the RBANS index scores are converted to classifications including Very Superior (130 and above), Superior (120-129), High Average (110-119), Average (90-109), Low Average (80-89), Borderline (70-79), and Extremely Low (69 and below). A score of Extremely Low equates to severe cognitive impairment. The primary outcome measure will be analyzed using ANCOVA controlling for memantine/placebo, baseline RBANS, sex, age, and NMDAR status.

Secondary Outcome Measures:

1. Incidence of Treatment-Emergent Adverse Events [Time Frame: 12 weeks]

We will determine the safety of memantine as measured by treatment-emergent adverse events.

2. Polysymptomatic Distress Scale [Time Frame: 12 weeks]

The Polysymptomatic Distress (PSD) scale measures the effect of PSD over a range of pain-related clinical symptoms. The scale was derived from variables used in the 2010 American College of Rheumatology fibromyalgia criteria, modified for use in clinical research, and broadened to be applicable for patients not meeting fibromyalgia diagnostic criteria. The PSD score is calculated by summing two components, the Widespread Pain Index (WPI) and Symptom Severity Scale (SSS). The WPI is a count of painful nonarticular body regions, and the SSS is a symptom severity measure that includes fatigue, sleep, and cognitive problems.

3. Beck Depression Inventory [Time Frame: 12 weeks]

The Beck Depression Inventory (BDI) is a 21-item, self-report inventory that measures depression symptoms and attitudes. It takes approximately 10 minutes to complete and requires a fifth to sixth grade reading level to adequately comprehend the questions.

4. Hospital Anxiety and Depression Scale [Time Frame: 12 weeks]

The Hospital Anxiety and Depression Scale (HADS) is a self-assessment scale and was developed to detect states of depression, anxiety, and emotional distress among patients who were being treated for a variety of clinical problems. The scale has a total of 14 items, with responses being scored on a scale of 0-3 (3 indicates higher symptom frequencies). Scores for each subscale (anxiety and depression) range from 0 to 21, categorized as follows: normal 0-7, mild 8-10, moderate 11-14, and severe 15-21.

5. Systemic Lupus Erythematosus Disease Activity Index (SLEDAI)-2K [Time Frame: 12 weeks]

SLEDAI-2K is an updated version of the SLEDAI which was originally developed in 1985 as a clinical index to assess lupus disease activity in the preceding 10 days. It is a cumulative and weighted index of 24 different clinical and laboratory variables/disease descriptors, comprising 9 organ systems. The Investigator will assess disease descriptors on the SLEDAI-2K collection sheet (e.g., arthritis, myositis, alopecia, rash, mucosal ulcers, etc.).

6. Patient Global Impression of Change [Time Frame: Endpoint (Visit 4)]

Participants will answer the standard question, "Considering all the ways your health affects you, how are you doing since the beginning of your treatment?" Answers include very much worse, much worse, worse, unchanged, improved, much improved, and very much improved.

7. RBANS Subscales [Time Frame: 12 weeks]

Our primary outcome is the RBANS Total Index Score, which is the sum of several subscales/tests. For a secondary outcome, we will look at each subscale/test individually to see if there is a trend for any one test in particular. The subscales are all scored the same (40-160) and include immediate memory, delayed memory, visuospatial/constructional, language, and attention.

Eligibility Criteria

18 Years to 60 Years (Adult)

Inclusion Criteria:

1. Meet American College of Rheumatology (ACR) criteria for SLE
2. Report NPSLE symptoms on the screening survey recommended by EULAR guideline but limited to the psychiatric manifestations questions
3. Score ≤85 on the RBANS total index (≤1 SD below the normative mean of 100)

Exclusion Criteria:

1. Male and female subjects <18 or >60 years
2. Change in medication that may affect mood or cognition including prednisone, antidepressant medications, or stimulants within the last 4 weeks
3. Regular (daily) use of opioids or other drugs of abuse including heavy alcohol or marijuana use
4. Metabolic derangement defined as liver function tests >3× upper limit of normal or severe renal disease defined as calculated creatinine clearance <30 mL
5. Severe psychiatric disease including schizophrenia, psychosis, suicidal depression
6. Other factors which in the opinion of the investigator could potentially impact the study outcomes (e.g., underlying disease, medications, history)* or prevent the participant from completing the protocol (poor compliance or unpredictable schedule)

7. Inability or refusal to give informed consent for any reason including a diagnosis of dementia or significant cognitive impairment**
8. Patients who are pregnant
9. Patients who are enrolled in other investigational drug studies Example 4

NR2 Antibody Effect on Calcium Flux in iPSC (CC-3) Cells

Figure 3:
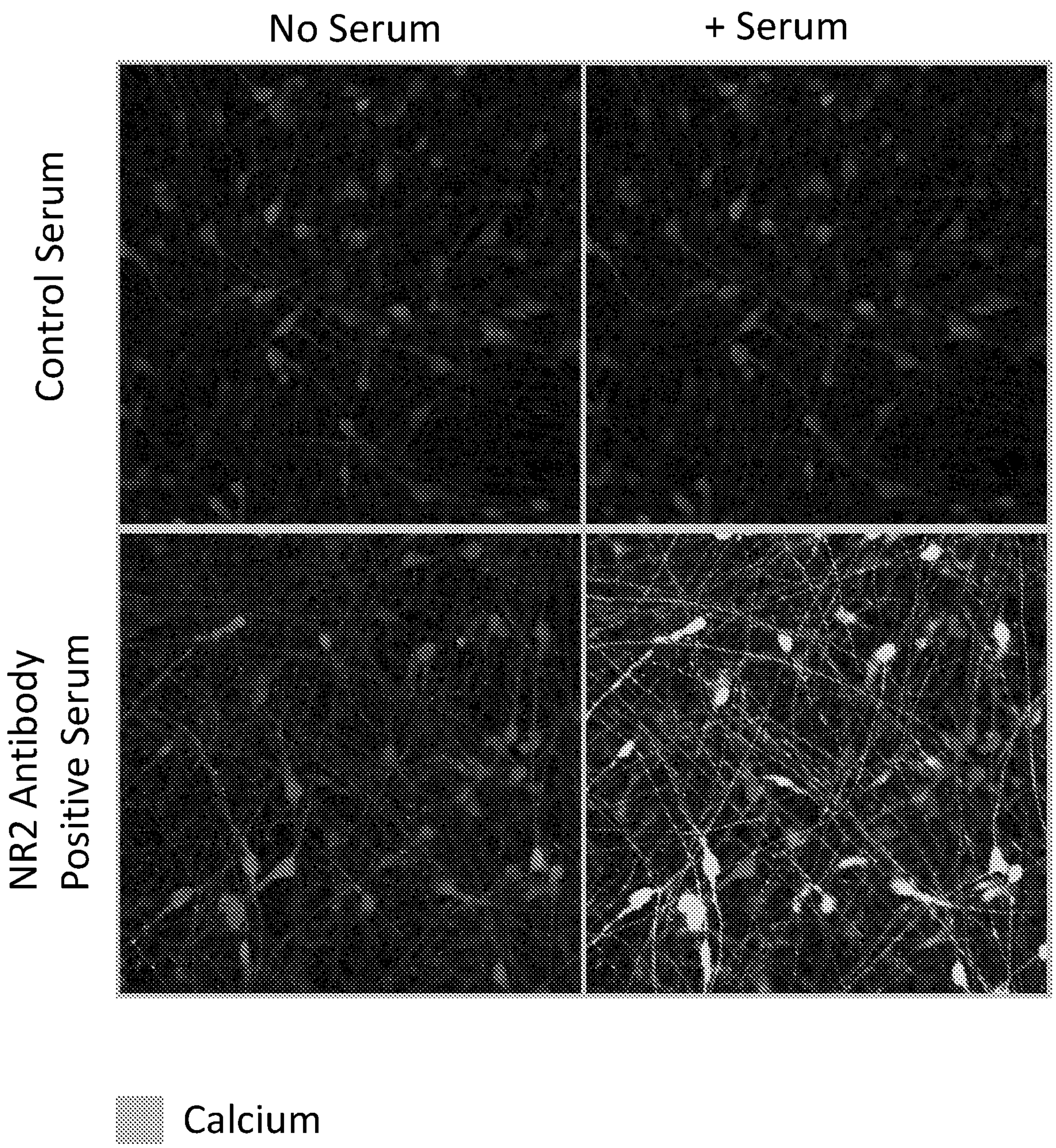
FIG. 3 shows calcium flux in human neurons differentiated from the CC-3 iPSC cell line following treatment with control or NR2 antibody positive serum. Increased calcium flux may indicate neuronal damage or dysfunction.

Human iPSC (CC-3) cells were cultured and differentiated using sequential differentiation media containing small molecule growth factors and activators for 15 days, as described by Qi et al. *Nat Biotechnol.* 2017; 35(2): 154-163. On day 16, the calcium indicator Fluo-4 was added to the cells. Three minutes following the addition of Fluo-4, a pre-image was taken by fluorescent microscopy. Control or NR2 antibody containing serum was then added to the cells at a 1:50 dilution. The cells were fixed with 4% PFA and imaged by fluorescent microscopy. Increased green intensity indicates increased calcium flux. The results are shown in FIG. 3.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating neuropsychiatric systemic lupus erythematosus (NPSLE) or systemic lupus erythematosus (SLE) with neurological manifestations in a human subject in need of treatment, the method comprising:
administering to the subject 25 mg/day to 40 mg/day of memantine or a pharmaceutically acceptable salt thereof.

2. The method of claim 1, wherein the subject exhibits one or more of the following symptoms: seizures, psychosis, epilepsy, a cerebrovascular event, lesion of cranial nerves, motor disturbances, quantitative alterations of consciousness, cognitive dysfunction, headache, peripheral neuropathy, aseptic meningitis, demyelinating syndrome, movement disorder, myelopathy, acute confusional state, anxiety disorder, mood disorder, acute inflammatory demyelinating, polyradiculoneuropathy, autonomic disorder, myasthenia gravis, cranial neuropathy, plexopathy, polyneuropathy, aphasia, and/or fatigue.

3. The method of claim 1, wherein the subject has a mutation in the ionotropic glutamate receptor NMDA type subunit 2A (GRIN2A) gene.

4. The method of claim 3, wherein the mutation results in a T141M amino acid substitution in the ionotropic glutamate receptor, NMDA 2A (GluN2A).

5. The method of claim 1, wherein the subject expresses autoantibodies to ionotropic glutamate receptor, NMDA 2A (GluN2A); and
wherein the autoantibodies are antibodies to the NR2A subunit(s) DWDYS (residues 283-287) and/or DWEYS of NMDAR.

6. The method of claim 1, wherein the pharmaceutically acceptable salt of memantine is memantine hydrochloride.

7. The method of claim 1, wherein the subject expresses autoantibodies to ionotropic glutamate receptor, NMDA 2A (GluN2A) and/or anti-ds DNA antibodies that cross react with one or more subunits of the NMDA receptor and has cognitive impairment.

8. The method of claim 7, wherein the method further comprises, before the administration of memantine:
obtaining a sample from the subject; and
detecting autoantibodies to GluN2A and/or anti-ds DNA antibodies that cross react with one or more subunits of the NMDA receptor in the sample.

9. The method of claim 1, wherein the method comprises administering to the subject 30 mg/day to 40 mg/day of memantine or a pharmaceutically acceptable salt thereof.

* * * * *